United States Patent [19]

Teeple

[11] Patent Number: 4,715,366
[45] Date of Patent: Dec. 29, 1987

[54] SURGICAL SHIELD

[76] Inventor: Edward Teeple, 641 Ridgefield Ave., Pittsburgh, Pa. 15216

[21] Appl. No.: 853,903

[22] Filed: Apr. 21, 1986

[51] Int. Cl.[4] ............................................. A61F 13/00
[52] U.S. Cl. ............................... 128/132 D; 128/303.1
[58] Field of Search ............ 128/132 R, 132 D, 303.1; 604/385.1; 5/482, 483, 502

[56] References Cited

U.S. PATENT DOCUMENTS

| | | | |
|---|---|---|---|
| 3,809,077 | 5/1974 | Hansen | 128/132 D |
| 4,024,862 | 5/1977 | Collins | 128/132 D |
| 4,450,845 | 5/1984 | Engel | 128/132 R X |
| 4,508,776 | 4/1985 | Smith | 5/482 X |
| 4,520,814 | 6/1985 | Weeks | 128/303.1 |

FOREIGN PATENT DOCUMENTS

| | | | |
|---|---|---|---|
| 2229521 | 1/1974 | Fed. Rep. of Germany | 5/483 |
| 3322981 | 1/1985 | Fed. Rep. of Germany | 128/303.1 |

*Primary Examiner*—Robert A. Hafer
*Assistant Examiner*—Kathleen J. D'Arrigo
*Attorney, Agent, or Firm*—Reed Smith Shaw & McClay

[57] ABSTRACT

A surgical shield for use during surgical procedures in which lasers are utilized and which comprises a fabric inner sheet interpositioned between a pair of coextensive metal foil sheets. The three sheets are attached together at their peripheries.

6 Claims, 3 Drawing Figures

SURGICAL SHIELD

FIELD OF THE INVENTION

The present invention relates to a surgical shield or blanket, and, in particular, to an aluminized blanket useful in protecting patients during surgical procedures involving lasers and in protecting anesthesia circuits from exposure to laser radiation.

BACKGROUND OF THE INVENTION

It is becoming more common to use lasers to perform various surgical techniques. As is well known, the radiation from such lasers must be confined to the operative area, however, it is equally well known that it is difficult, if not impossible, to prevent the occurence of stray radiation in the operating rooms. Operating room personnel have begun wearing protective eye glasses and patients undergoing such procedures have been provided moistened gauze over the eyes, More recently, a surgical eye mask has been developed to protect the patient's eyes during laser surgery, see U.S. patent application Ser. No. 661,120.

The need for better protection for both the patient and the operating personnel during laser surgery has become apparent. The patient may be injured by direct exposure to the beam on the skin causing burns or flesh wounds or opthalmic injury or loss of vision if the eyes were to become accidentally exposed. The patient is highly at risk during the anesthesia, if such is a general anesthesia, since the patient is unable to alert the surgical personnel of the occurence of an injury. The current use of wet towels is not a satisfactory method, because the sterile plastic sheet below the towels can be ignited by the laser beam, bacterial contamination may occur when plastic sheets are not used, and there is a potential of fire from towels which have not been remoistened during the operative procedure.

The problems encountered by patients are also encountered by the operating room personnel, but to a much lesser extent. The operating room personnel to some extent can avoid continued contact from the beam by stepping out of its path or alerting the user. Nevertheless, it is not always possible to remove oneself from the path of the beam and even short exposures may cause injury.

Another problem encountered is the exposure of the anesthesia machine and circuits to the laser radiation. The anesthesia circuit often lies near the operative field, especially during neurosurgery or during ENT surgery. Typically, these circuits have been wrapped in aluminum foil to deflect the stray radiation. However, such wrapping prevents the anesthesiologist from observing these circuits. Further, aluminum foil is very difficult to work with, especially around the endotracheal tube.

Accordingly it is an object of the present invention to provide a surgical shield to protect patients, operating room personnel, and anesthesia circuit/machines during laser surgery. It is a further object of the invention to provide a shield for anesthesia circuits which provides a snug fit over the circuit but also affords the anesthesiologist an easier means to view of the circuits during the operation.

SUMMARY OF THE INVENTION

Generally, the present invention provides a blanket or shield which is comprised of at least one first and at least one second outer metallic sheets, preferably of an aluminum foil, which has sandwiched therebetween a woven textile fabric, such as cotton gauze. In an alternate embodiment, nonwoven fabrics or sheets may be usefully substituted for the more fragile textile fabrics. The outer periphery of the first and second sheets is fastened together to interpose therebetween the gauze and to form the blanket. Eyelets are preferably positioned along an edge or outer portion of the periphery so that it can be hung in the operating room to partially isolate the laser beam from the operating room personnel.

In another embodiment of the invention, the blanket is provided with concentric precut or perforated openings to afford the surgeon access to the operative field. Any configuration or design of perforation can be used, but concentric circles or ellipses are most desirable for the typical laser operation. In this embodiment it is desirable to provide an adhesive coating on one side of the blanket to prevent movement on the patient's body.

For use in protecting an anesthesia circuit, the above described shields can be utilized. However, it is more desirable to form the blanket or shield with an VELCRO-type fastener material at the distal and along the sides to allow the shield to snugly fit over the circuit. Additionally, it is desirable to wrap the shield over the circuit in a "c"-configuration and to provide either fixed or removable straps to provide a view to the circuits. These and other advantages of the present invention will become apparent from a perusal of the following detailed description of the presently preferred embodiments of the invention taken in connection with the accompanying drawings.

PRESENTLY PREFERRED EMBODIMENTS

Figure 1:
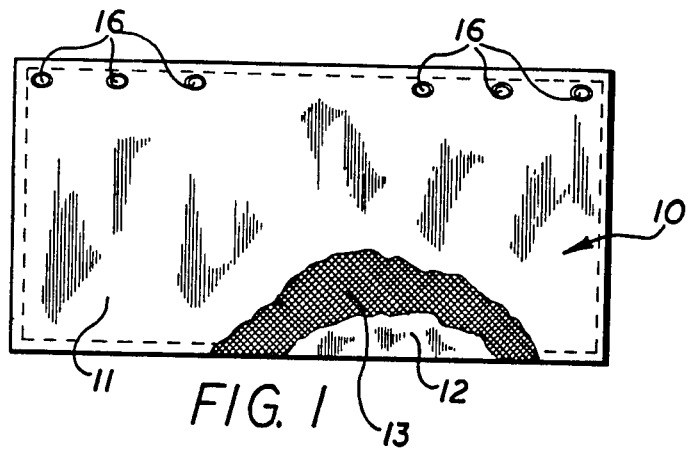
FIG. 1 is an elevation of the shield the present invention, shown in partial break away, for patient or operating room personnel use during laser surgery; (a personnel drape.)

Referring to FIG. 1, laser shield 10 of the present invention is shown. Laser shield 10 comprises first and second metallized sheets 11 and 12, respectively. Interposed between first and second sheets 11 and 2 is an inner fabric 13, Fabric 13 is preferably a cotton gauze, if a woven textile is elected, but may be any sterilizable, pliable fabric, such as nonwoven sheets composed of elastomeric materials, like pliable polyolefin, such as isotactic polypropylene. Typically, the plastic interliner has a thickness of about one mil, so it conforms readily to manipulation of its contour by the surrounding metallic foil. If the foil is too thin, it will tend toward heat deforming, and if excessively heavy, it will tend toward cracking with handling. Under actual testing with surgical lasers, this device has been shown to be resistant to melting or ignition with flame within power limits used for clinical laser surgery.

High density polyethylene, and copolymers of polypropylene and polyethylene, may also be usefully employed as the inner layer, the major parameter is that the polyolefin, in thicknesses up to a few mils, be drapable (hand moldable), while within the meltable sheets it retains its conformation during the normal range of temperatures created on the sheet surface by laser beam impingement.

Outer sheets 11 and 12 are preferably formed from aluminum foil having a thickness of approximately 3 mils. The thickness of the foil is not critical, but it is to be understood that if the foil is too thin it is subject to being easily damaged during use, on the other hand, if the foil is exceptionally heavy, it become unwieldly and unmanageable on the operating table or patient. Also, the foil may have a matte finish or surface. Many applications having a matte finish may be preferable for beam dispersion.

Shield 10 can be used to cover the patient to protect the patient from laser radiation during surgery as well as over the anesthesia circuits. In addition to use by patients, the shield can be used by operating room anesthesia personnel. In the latter case it is desirable to include eyelets 16 along portions of the periphery of the shield 10. Use of eyelets 16 permits shield 10 to be strategically placed in the operating room to isolate the laser and its beam from the operating room anesthesia personnel. It can be appreciated that other forms of fasteners or hangers can achieve the same purpose.

Figure 3:
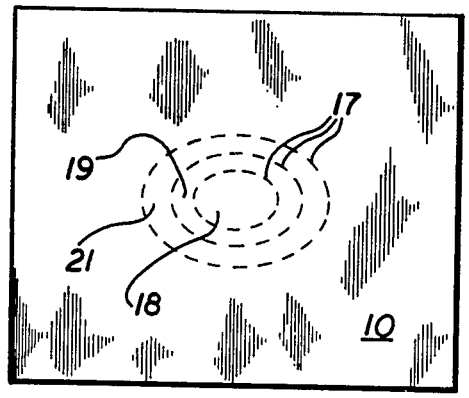
FIG. 3 is an elevation of the blanket for patient use and shows precut operative openings or perforations (an operating field drape).

Another feature of shield 10 is shown in FIG. 3, in which precut perforations 17 are provided. Preferably, perforations are concentrically arranged circles or ellipses which the surgeon can remove to expose an operating field on the patient's body. Removing the innermost area 18 to the outermost area 21 exposes an increasingly larger field in which to operate. Where the shield is to be used to protect a patient during laser surgery, it is desirable to include on the side facing the patient an adhesive to prevent movement of shield during the operative procedure. Further, in such surgical procedures, it is preferable to utilize only one sheet of foil rather than the multi-ply shield described above, that is, the foil is positioned only on the side exposed to the laser beam.

Figure 2:
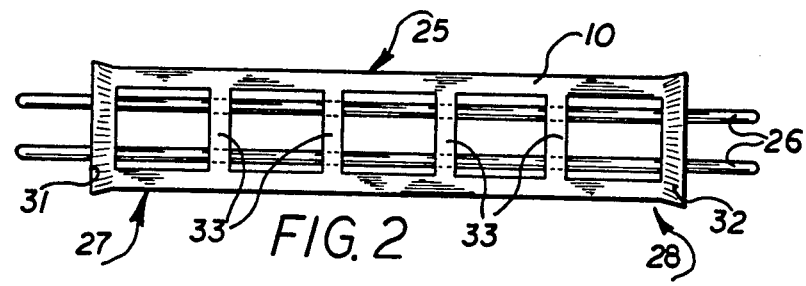
FIG. 2 is a side elevation of the present invention and for shield anesthesia circuits.

With reference to FIG. 2, shield 10 is formed in a sheath configuration 25 for protection of anesthesia circuits 26. Preferably sheath 25 includes at its distal and proximal sides 27 and 28, respectively, VELCRO-type strips 31 and 32. Strips 31 and 32 permit sheath 25 to engage circuits 26 and also permit sliding movement along the length of the circuits. In the preferred embodiment, strips 33 are provided to attach the peripherial edges of shield 10 together. By use of such strips 33, the circuits 26 can be easily viewed by the anesthesiologist during the operation.

While presently preferred embodiments of the invention have been shown and described in particularity, it may be otherwise embodied within the scope of the appended claims.

What is claimed is:

1. A malleable, lightweight surgical shield for use in an operating room and on a patient during laser procedures comprising:
   a. a non-woven fabric polymeric inner sheet,
   b. first and second aluminum foil sheets having a matte surface respectively positioned over each side of said fabric inner sheet to coextensively interpose said fabric sheet between said foil sheets; and
   c. means for attaching together the respective foil and fabric sheets.

2. A surgical shield as set forth in claim 1, wherein said periphery includes a plurality of eyelets to support said shield.

3. A surgical shield as set forth in claim 1, wherein said foil sheets and fabric sheet includes at least one bounded perforation for removing the area bounded thereby to expose an operative field.

4. A surgical shield as set forth in claim 1, wherein said foil is aluminum and said inner sheet comprises a polyolefin plastic.

5. A surgical shield as set forth in claim 1, wherein the polyolefin inner sheet comprises polypropylene (polyethylene).

6. A shield as set forth in claim 1 adapted for shielding anesthesia circuits provided with Velcro-type fastener strips disposed about said circuits for easier viewing thereof.

* * * * *